(12) United States Patent
Kiani

(10) Patent No.: US 12,272,445 B1
(45) Date of Patent: Apr. 8, 2025

(54) AUTOMATED MEDICAL CODING

(71) Applicant: Masimo Corporation, Irvine, CA (US)

(72) Inventor: Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 153 days.

(21) Appl. No.: 17/112,010

(22) Filed: Dec. 4, 2020

Related U.S. Application Data

(60) Provisional application No. 62/944,268, filed on Dec. 5, 2019.

(51) Int. Cl.
| | |
|---|---|
| *G16H 40/20* | (2018.01) |
| *A61B 5/00* | (2006.01) |
| *G06N 20/00* | (2019.01) |
| *G06Q 10/10* | (2023.01) |
| *G06Q 40/08* | (2012.01) |
| *G16H 10/60* | (2018.01) |
| *G16H 15/00* | (2018.01) |
| *G16H 40/67* | (2018.01) |
| *G16H 50/20* | (2018.01) |
| *G16H 50/70* | (2018.01) |
| *G16H 70/20* | (2018.01) |
| *G16H 70/60* | (2018.01) |

(52) U.S. Cl.
CPC ........... *G16H 40/20* (2018.01); *A61B 5/7267* (2013.01); *G06N 20/00* (2019.01); *G06Q 10/10* (2013.01); *G06Q 40/08* (2013.01); *G16H 10/60* (2018.01); *G16H 15/00* (2018.01); *G16H 40/67* (2018.01); *G16H 50/20* (2018.01); *G16H 50/70* (2018.01); *G16H 70/20* (2018.01); *G16H 70/60* (2018.01)

(58) Field of Classification Search
CPC ........ G16H 40/20; G16H 10/60; G16H 15/00; G16H 40/67; G16H 50/20; G16H 50/70; G16H 70/20; G16H 70/60; A61B 5/7267; G06N 20/00; G06Q 10/10; G06Q 40/08
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |

(Continued)

OTHER PUBLICATIONS

US 2022/0192529 A1, 06/2022, Al-Ali et al. (withdrawn)

(Continued)

*Primary Examiner* — Amber A Misiaszek
(74) *Attorney, Agent, or Firm* — Knobbe, Martens, Olson & Bear, LLP

(57) ABSTRACT

Systems and methods for improving reimbursement rates from payors for services or procedures provided by a medical care provider are disclosed herein. In some examples, reimbursement can be improved by improving the accuracy of medical coding of services and diagnosis codes through the use of machine learning techniques. In some examples, the system can suggest codes more likely to get reimbursed by a payor through analysis of patient data and/or insurance information. In some examples, the system can determine a likelihood of reimbursement through analysis of patient data and/or insurance information.

19 Claims, 9 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,626,144 A * | 5/1997 | Tacklind ............. A61B 5/0871 600/529 |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Ai-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Ai-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |

(56) References Cited

U.S. PATENT DOCUMENTS

| | | | |
|---|---|---|---|
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | Macneish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |

(56) References Cited

U.S. PATENT DOCUMENTS

| | | |
|---|---|---|
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Ai-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,796,390 B2 * | 10/2020 | Kapit .................. G16H 30/20 |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| 11,315,196 B1 * | 4/2022 | Narayan .............. G06F 18/2193 |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |

(56) References Cited

U.S. PATENT DOCUMENTS

| | | |
|---|---|---|
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 2001/0034477 A1 | 10/2001 | Mansfield et al. |
| 2001/0039483 A1 | 11/2001 | Brand et al. |
| 2001/0051764 A1* | 12/2001 | Bardy .................. A61B 5/021 600/300 |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2003/0212579 A1* | 11/2003 | Brown .................. A61B 5/411 600/300 |
| 2004/0106163 A1 | 6/2004 | Workman, Jr. et al. |
| 2005/0020903 A1* | 1/2005 | Krishnan .............. G16H 50/20 600/407 |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0004505 A1* | 1/2008 | Kapit .................... G16H 10/60 600/300 |
| 2008/0004904 A1* | 1/2008 | Tran .................... G16H 40/67 340/286.07 |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0137297 A1 | 6/2011 | Kiani et al. |
| 2011/0169644 A1 | 7/2011 | Muhsin et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0297348 A1* | 11/2013 | Cardoza ................ G16H 40/20 705/3 |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106020 A1* | 4/2015 | Chung .................. G16H 40/67 702/19 |
| 2015/0106121 A1 | 4/2015 | Muhsin et al. |
| 2015/0134346 A1* | 5/2015 | Hyde .................... G06Q 10/10 705/2 |
| 2016/0196388 A1 | 7/2016 | Lamego |
| 2016/0220198 A1* | 8/2016 | Proud .................. A61B 5/0022 |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0025116 A1* | 1/2018 | Carrington ............ G16H 10/60 705/3 |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |

(56) References Cited

U.S. PATENT DOCUMENTS

| | | |
|---|---|---|
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Ai-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kian |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

OTHER PUBLICATIONS

US 2024/0016391 A1, 01/2024, Lapotko et al. (withdrawn)

Xiong, Maria L. "Assuring Consistent and Compliant Data Capture for Coding and Reimbursement." The College of St. Scholastica, 2012. Ann Arbor (Year: 2012).*

* cited by examiner

AUTOMATED MEDICAL CODING

CROSS-REFERENCE TO RELATED APPLICATIONS

This application is claims priority to U.S. Provisional App. No. 62/944,268, filed on Dec. 5, 2019, entitled "AUTOMATED MEDICAL CODING", the entire contents of which are incorporated by reference and made a part of this specification.

FIELD

The present disclosure generally relates to systems and methods to facilitate improved medical coding and data analysis for submission to insurance providers.

BACKGROUND

Medical services and procedures are coded into alphanumerical codes in order to transmit information regarding an applied medical service or procedure to a payor, such as a patient's insurance provider. Medical coding is often done by medical coding professionals using notes provided by a patient's clinician. However, errors in a clinician's notes can result in incorrectly coded services or procedures. Additionally, specialized knowledge of the rules and regulations of a payor are required to appropriately code services and procedures.

SUMMARY

Further details of features, objects, and advantages of the disclosure are described below in the detailed description, drawings, and claims. Both the foregoing general description and the following detailed description are exemplary and explanatory and are not intended to be limiting as to the scope of the disclosure.

In some examples, a system for improving accuracy of medical coding can include a non-transitory memory configured to store a machine learning classifier and one or more hardware processors in communication with the non-transitory memory. The machine learning classifier can be configured to identify a service code associated with a threshold probability of reimbursement by a payor. The machine learning classifier can be trained using historical reimbursement data associated with a plurality of patient records. The one or more hardware processors configured to receive patient information comprising at least one of: physiological parameters obtained from the at least one physiological sensor and clinician input, wherein the clinician input comprises diagnosis data or treatment data; access insurance information associated with the patient comprising at least one of: plan coverage and a plurality of service codes; identify a diagnosis code associated with the patient based on the patient information; and analyze the patient information and the insurance information to determine, using the at least one machine learning classifer, at least one service code associated with a threshold probability of reimbursement by the payor.

BRIEF DESCRIPTION OF THE DRAWINGS

Throughout the drawings, reference numbers are re-used to indicate correspondence between referenced elements. The following drawings and the associated descriptions are provided to illustrate embodiments of the present disclosure and do not limit the scope of the claims.

The drawings illustrate the design and utility of various embodiments of the present disclosure. It should be noted that the figures are not drawn to scale and that elements of similar structures or functions are represented by like reference numerals throughout the figures. In order to better appreciate how to obtain the above-recited and other advantages and objects of various embodiments of the disclosure, a more detailed description of the present disclosure briefly described above will be rendered by reference to specific embodiments thereof, which are illustrated in the accompanying drawings. Understanding that these drawings depict only typical embodiments of the disclosure and are not therefore to be considered limiting of its scope, the disclosure will be described and explained with additional specificity and detail through the use of the accompanying drawings in which.

DETAILED DESCRIPTION

In some medical billing environments, a clinician may perform a diagnostic analysis on a patient. The clinician may input the results of the diagnostic analysis into an input device that may store the information in an electronic medical record (EMR) associated with the patient. The diagnostic analysis may be associated with a diagnosis code. The diagnosis code can be an alphanumerical code identifying one or more diseases, disorders, symptoms, or other medical situations. A clinician may also apply a treatment on a patient. The clinician may input the treatment into an input device that may store the information in the EMR associated with the patient. The treatment may be associated with a service or procedure code. The service code can be an alphanumerical code identifying one or more medical services or procedures performed.

In some cases, the clinician or a medical coder may manually input a diagnosis code or service code, which can result in administrative inefficiencies due to the reliance on the understanding, memory, and accuracy of the clinician in entering codes. This inefficiency can result in costly errors when the codes get processed for medical billing. In order to solve these inefficiencies, some medical billing environments utilize manual reviewers. The diagnosis code, the service code and other information in the EMR may be analyzed by a medical coder who cleans the data before sending the service code data to a payor, such as the patient's insurance carrier, for billing purposes. The medical coder may be trained to review the inputs for billing purposes.

However, a medical coder may not be able to clean data with sufficient accuracy and specificity to obtain a successfully payed claim. This can be due to user error, poor documentation by the clinician of services provided, poor training or difficulty in access to a provider or payor for purposes of clarification of coding information, particulars of a patient's insurance plan (that, for example, does not allow for a particular service, duplicate or otherwise fraudulent billing, lack of medical necessity, or other payor or insurance plan specific items. Thus, in many cases, it can be difficult for a coder or clinician to know what an insurer will or won't pay for even after review and cleaning of the data. Thus, merely cleaning the data may not provide optimal reimbursements to clinical care providers, such as hospitals, doctor's offices, or other healthcare providers. What is needed is a system to identify and predict accurate medical coding that will optimize reimbursements from payors to clinical care providers and removes or reduces sources of user error.

Figure 1A:
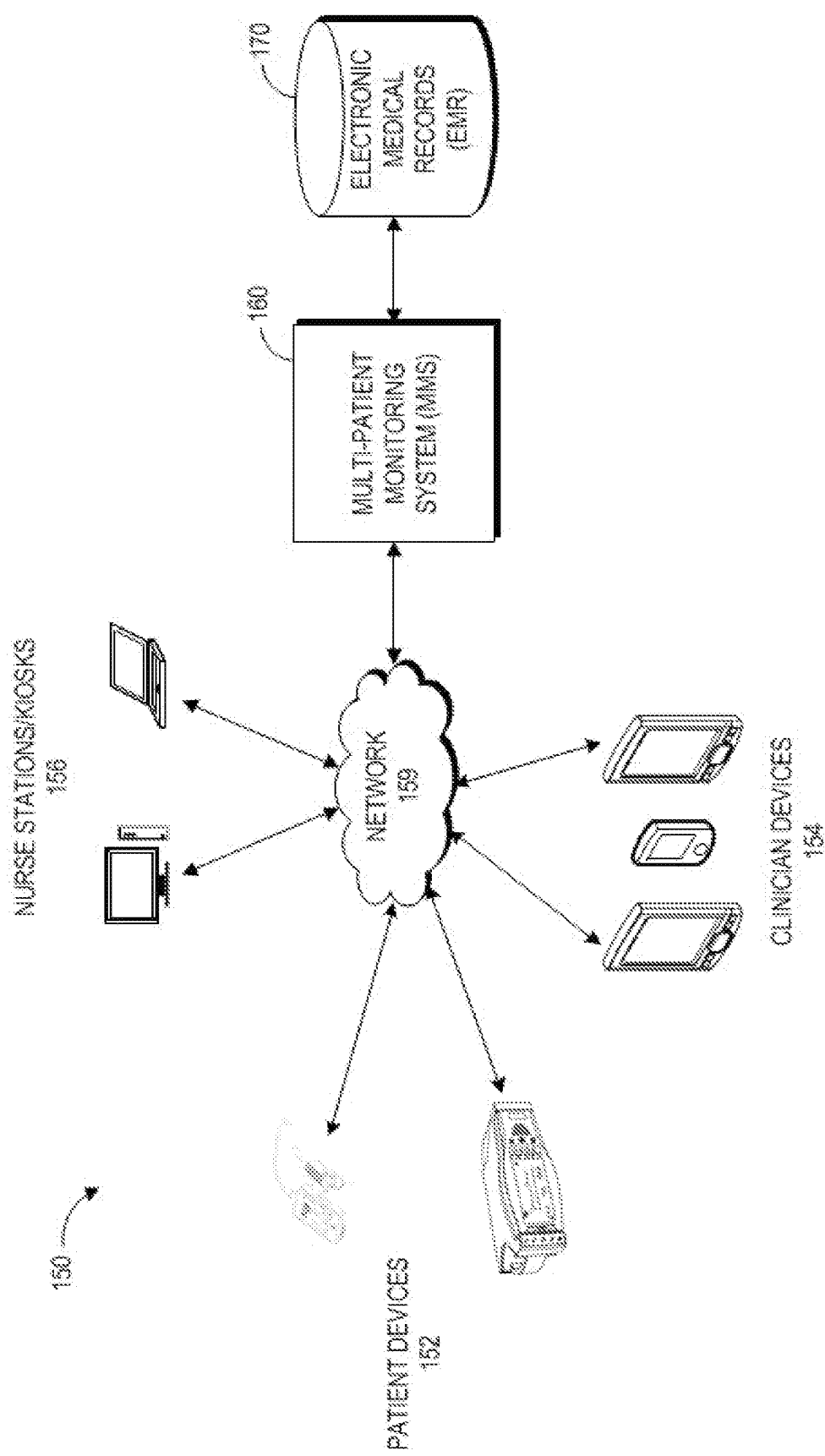
FIG. 1A depicts an example clinical computing environment.

Disclosed herein are systems and methods for improving reimbursement rates from payors for services or procedures provided by a medical care provider, such as a hospital or clinician. In some examples, reimbursement can be improved by improving the accuracy of medical coding of services and diagnosis codes through the use of machine learning techniques. In some examples, the system can suggest codes more likely to get reimbursed by a payor through analysis of patient data and/or insurance information. In some examples, the system can determine a likelihood of reimbursement for a code through analysis of patient data and/or insurance information. In some examples, the system may communicate directly with physiological monitors or other clinical care devices in order to provide, verify or suggest A. Example Patient Monitoring Environments FIG. 1A illustrates an example of a clinical computing environment 100 in which a medical coding system may be applied is shown. The clinical computing environment 100 may be implemented in one or more hospitals or other clinical facilities. Further, the clinical computing environment 100 can facilitate monitoring patients within their homes if such patients are using network-enabled monitoring equipment. Additional details of the example environment 100 are described in U.S. Patent Pub. No. 2015/0106121, titled "Alarm Notification System," filed Oct. 10, 2014 ("the '121 publication"), the disclosure of which is hereby incorporated by reference in its entirety. Any of the features described in the '121 publication can be implemented together with any of the features described herein.

In the clinical computing environment 100, various patient devices 102, clinician devices 104, and nurse's station systems or kiosks 106 can communicate over a network 109 with a multi-patient monitoring system (MMS) 110. The MMS 110 is an example of a remote server that can communicate with patient devices and clinician devices. The network 109 may include a local area network (LAN), a wide area network (WAN), a public network (such as the Internet), a private network, or any combination of the same. For instance, the network 109 can include a wireless and/or wired hospital network or a network that connects multiple clinical facilities.

The patient devices 102 may be any of the patient monitors or monitoring devices described herein and may include bedside monitors, ambulatory or mobile monitors, in-home monitors, and the like. The patient devices 102 can be point-of-care devices, such as bedside devices or patient-worn devices. The patient devices 102 can receive input from physiological sensors coupled with a patient and may measure parameters such as oxygen saturation or SpO2, respiratory rate, blood pressure, heart rate or pulse rate perfusion, other blood gas parameters, brain activity, brain oxygen saturation, any of the other parameters described herein, and the like. The patient devices 102 can provide information about a patient's status, including current values of physiological parameters, waveforms, trend values, and historical values of physiological parameters over the network 109 to the MMS 110. The MMS 110 can in turn store this data in an electronic medical records (EMR) system 120.

In addition, the MMS 110 can provide this data to the nurse's station systems 106. The nurse's station systems 106 can include any type of computing device including, but not limited to, a desktop, laptop, tablet, phone or the like. The nurse's station systems 106 may also include clinical facility kiosks such as computers on wheels (COWs) (which may use laptop or tablet computers), which may be dispersed throughout a clinical facility. The nurse's station systems 106 can communicate with a plurality of patient devices 102 to receive information of a plurality of patients so that the nurse's station systems 106 can provide clinicians with the ability to monitor physiological parameter data for a plurality of patients.

The clinician devices 104 can include any mobile device, such as a laptop, tablet, cell phone, smartphone, personal digital assistant (PDA), or any other device. In some cases, the clinician devices can include desktop systems. In turn, the MMS 110 can send alarms or messages representing alarms to the nurse's station systems 106 and/or the clinician devices 104. Further, the patient devices 102 may have network capability that enables the patient devices 102 to send the alarm notifications over the network 109 to the MMS 110, the nurse's station systems 106 and/or to the clinician devices 104. Some alarms can include nonclinical alarms that may not represent that a physiological parameter has exceeded a threshold but instead may include information about a sensor that has been disconnected or otherwise has fallen off (often referred to as a probe-off condition), or a low battery of a patient device 152. Sensor disconnection or probe-off can be detected using any of a variety of techniques, some examples of which are described in U.S. Pat. No. 6,360,114, filed Mar. 21, 2000, titled "Pulse Oximeter Probe-off Detector," and U.S. Pat. No. 9,750,461, filed Dec. 20, 2013, titled "Acoustic Respiratory Monitoring Sensor with Probe-off Detection," the disclosures of which are hereby incorporated by reference in their entirety.

Figure 1B:
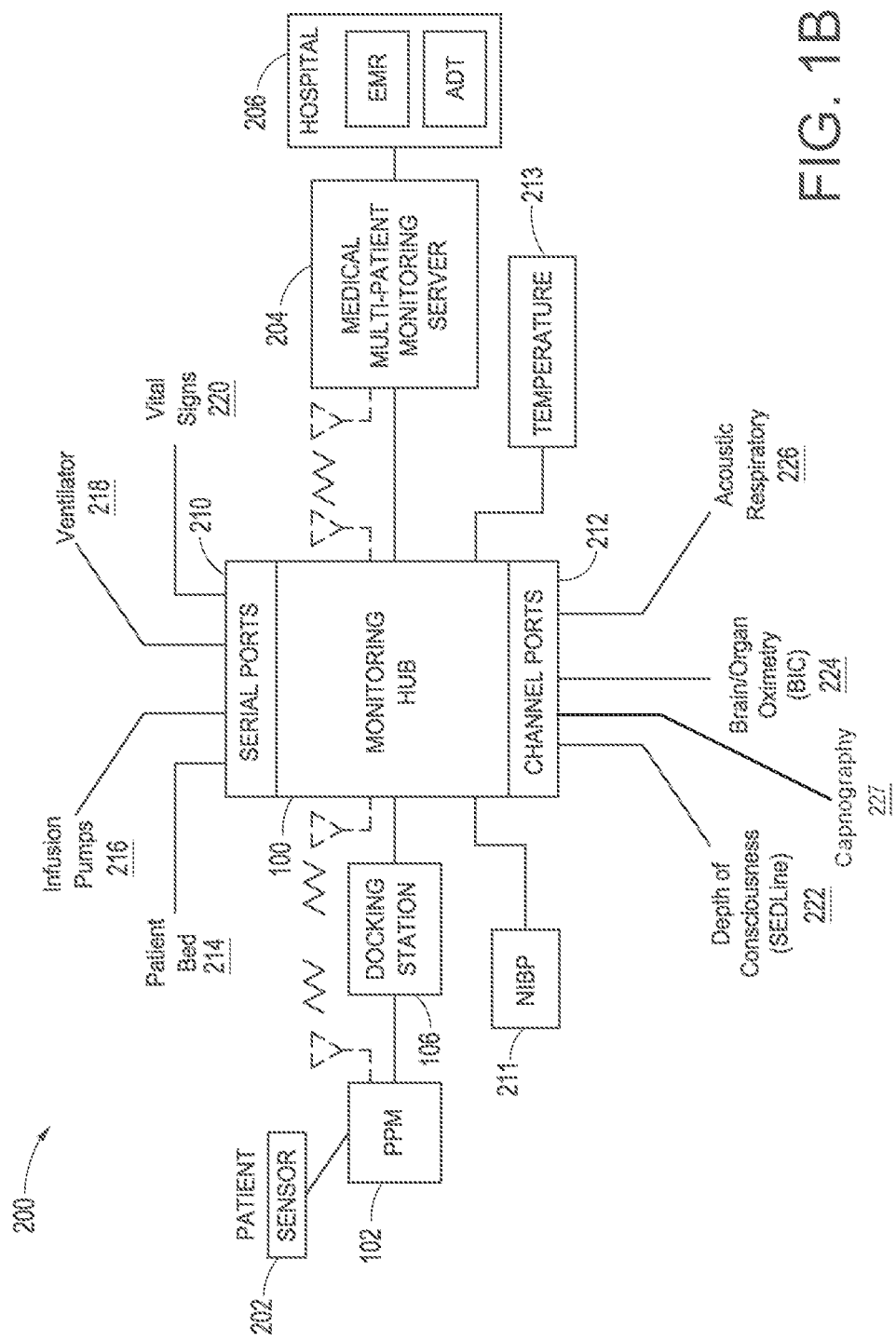
FIG. 1B illustrates a simplified block diagram of a patient monitoring environment.

FIG. 1B illustrates another simplified block diagram of a monitoring environment 200. As shown in FIG. 1B, the environment may include the portable patient monitor 102 communicating with one or more patient sensors 202, such as, for example, oximetry optical sensors, acoustic sensors, blood pressure sensors, respiration sensors or the like. Additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

The portable patient monitor 102 may communicate with the hub 100 through the docking station 106 when docked and wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140, which are hereby incorporated by reference in their entirety. In general, the server 204 communicates with caregiver backend systems 206 such as EMR or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 1B also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SedLineTM, other brain or organ oximeter devices 224, noninvasive blood pressure or acoustic devices 226, capnography devices 227, or the like. Channel device may include board-in-cable ("BIC") solutions where the processing algorithms and the signal processing devices that accomplish those algorithms are mounted to a board housed in a cable or cable connector, which may have no additional display technologies. The BIC solution outputs its measured parameter data to the channel port 212 to be displayed on the display 104 of hub 100. The hub 100 may advantageously be entirely or partially formed as a BIC solution that communicates with other systems, such as, for example, tablets, smartphones, or other computing systems.

Figure 1C:
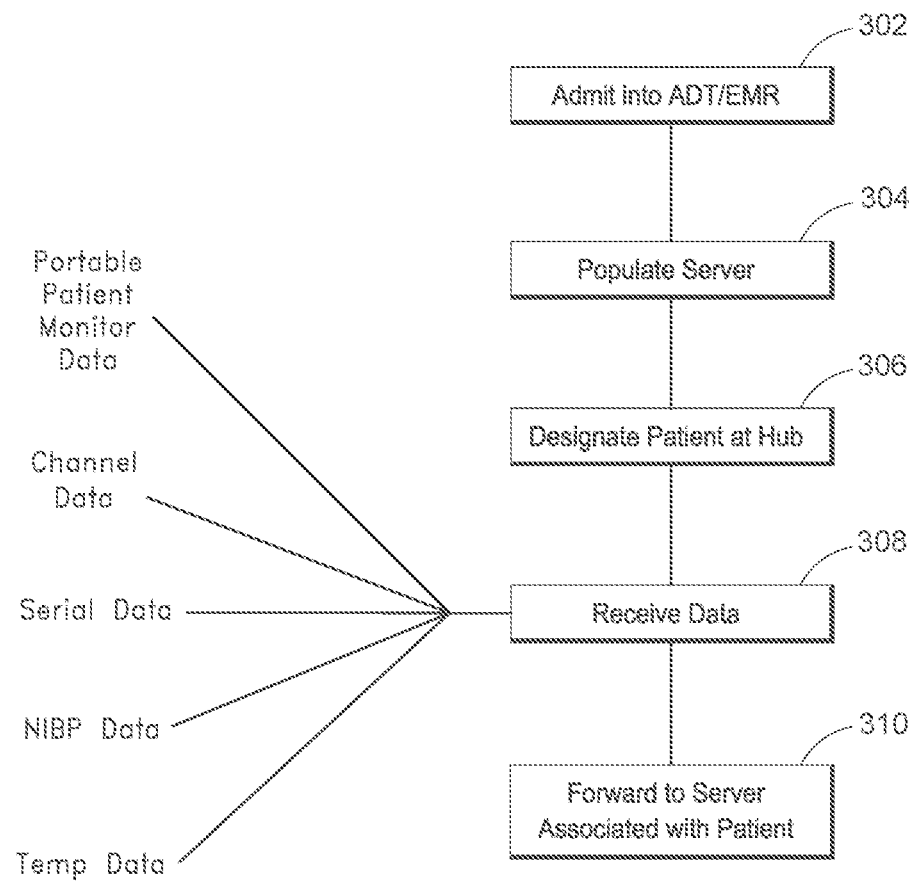
FIG. 1C illustrates a simplified patient data flow process.

FIG. 1C illustrates a simplified patient data flow process for data that may be utilized in a medical coding system. As shown, once a patient is admitted into the caregiver environment at step 302, data about the patient is populated on the caregiver backend systems 206. The server 204 may acquire or receive this information in step 304, and then make it accessible to the hub 100. When the caregiver at step 306 assigns the hub 100 to the patient, the caregiver simply looks at the presently available patient data and selects the particular patient being currently monitored. The hub 100 at step 308 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms. At step 310, some or the entirety of the received, processed or determined data is passed to the server 204.

B. Example Hardware

Figure 2A:
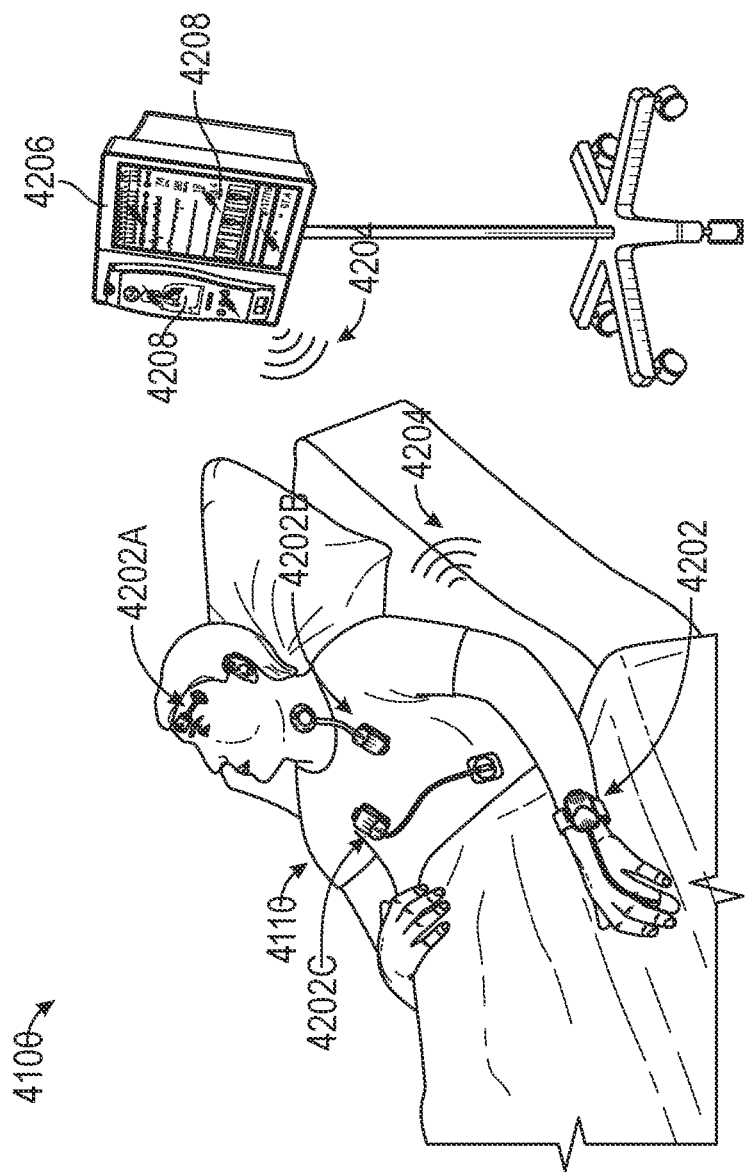
FIG. 2A illustrates a view of an example sensor system that may be part of a coding environment.
Figure 3A:
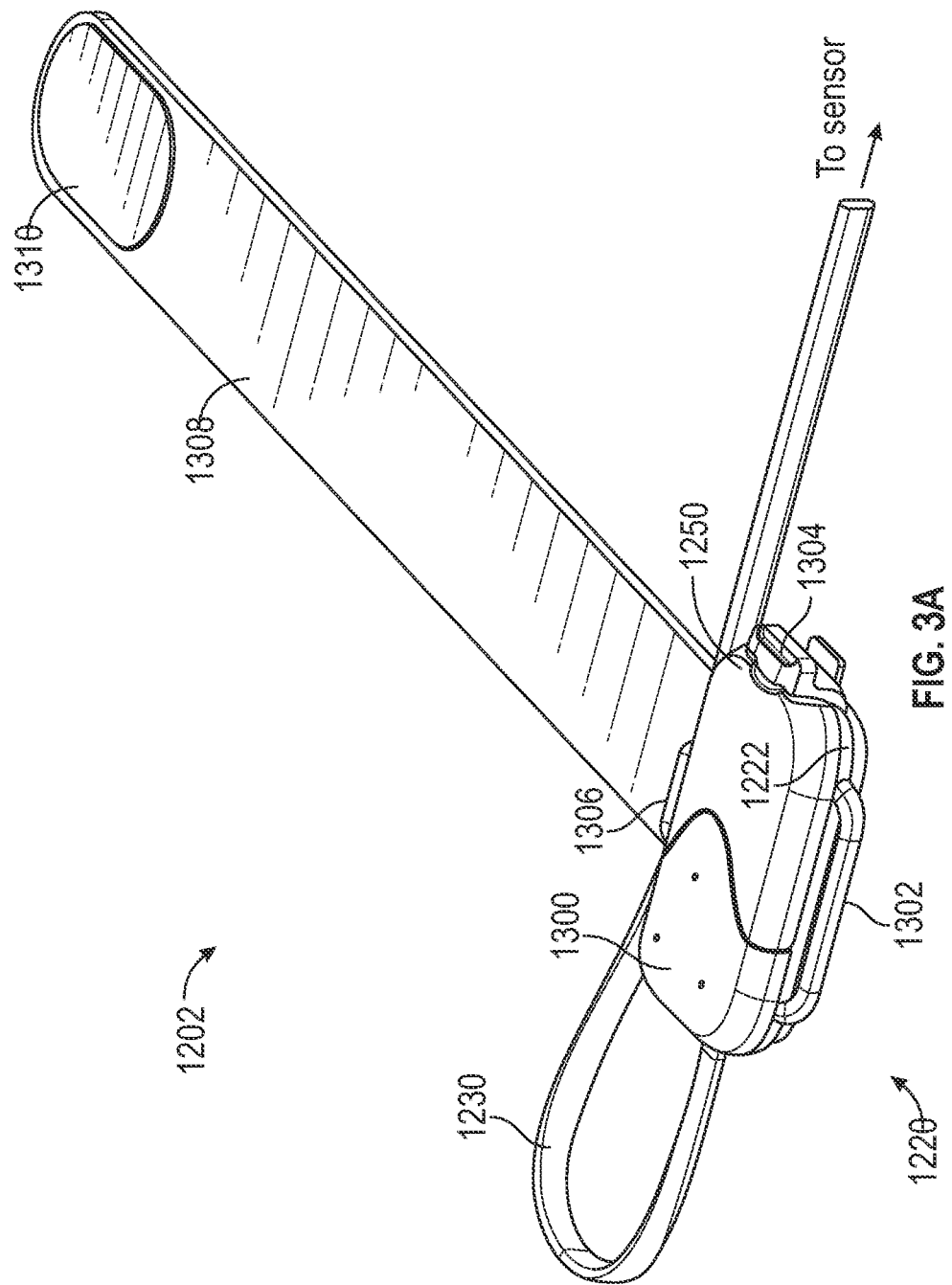
FIGS. 3A-3C illustrate different example sensor assemblies for collecting and transmitting patient physiological data to a computing device.
Figure 3B:
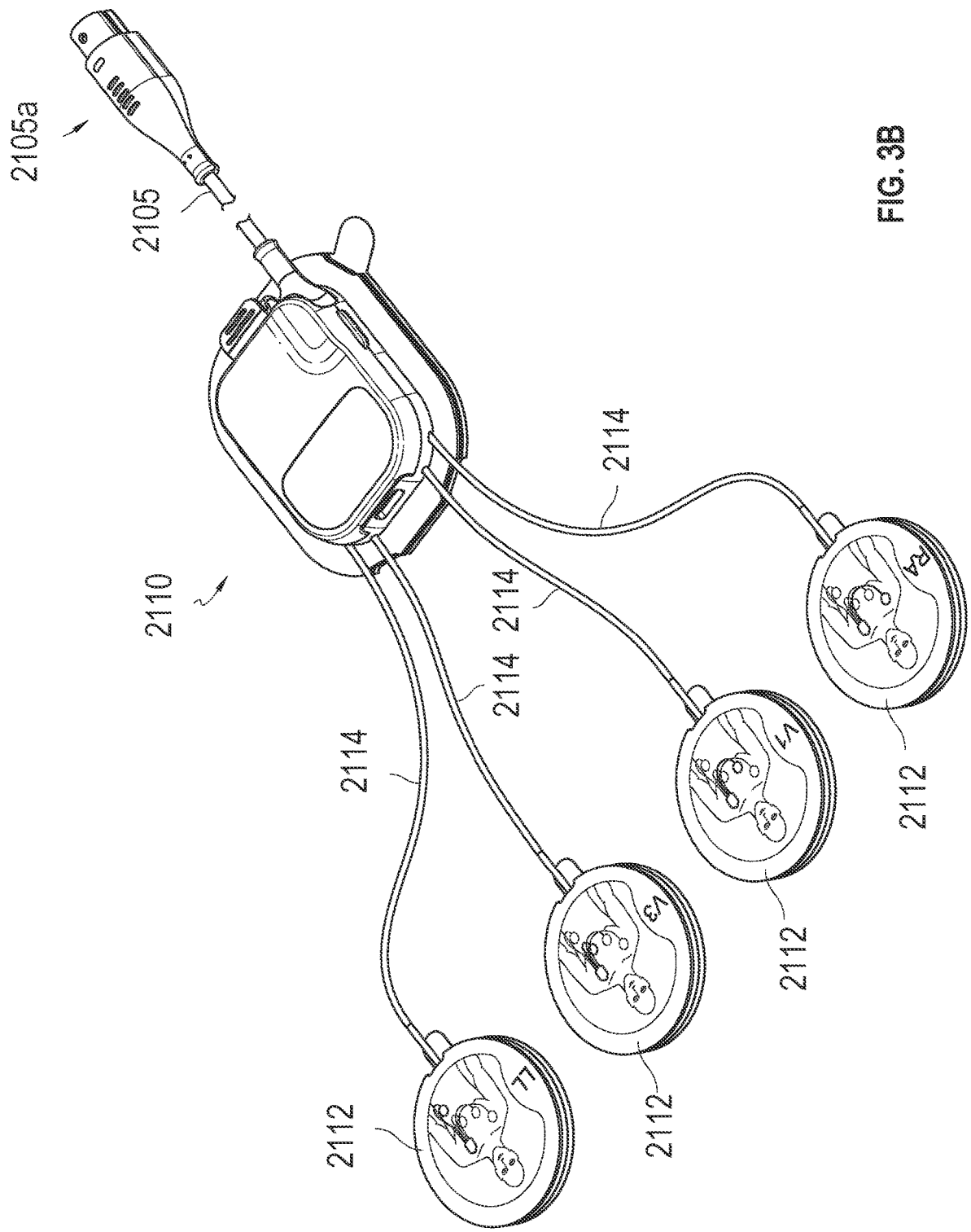
Figure 3C:
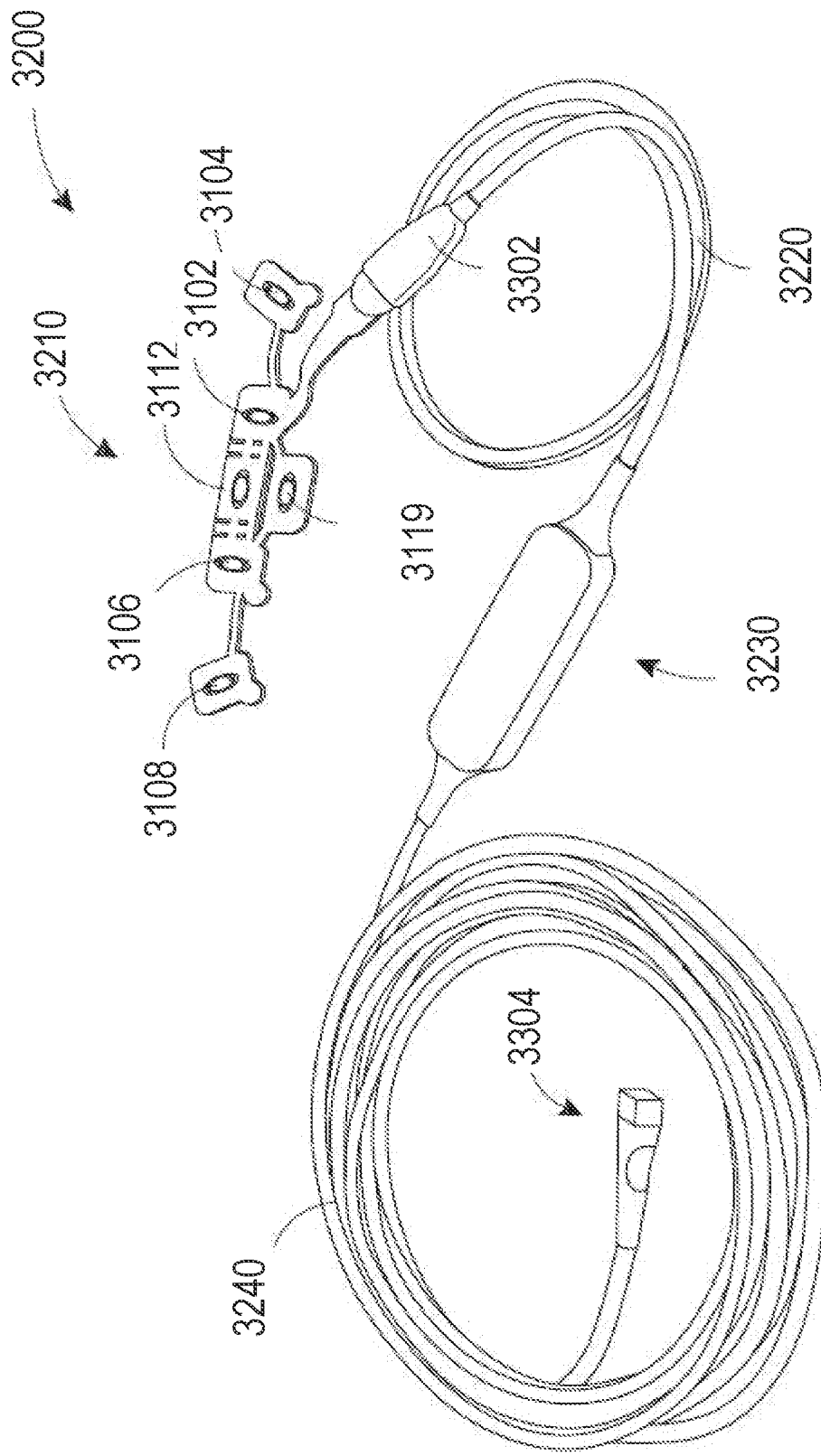

FIG. 2A illustrates an example sensor system that may be part of a medical coding environment 100. FIGS. 3A-3C illustrate example sensors that may be part of an example sensor system illustrated in FIG. 2A. For example, signals from one or more sensors or other devices in a sensor system may be used as input to an automated medical coding system.

As illustrated in FIG. 2A, a sensor system 4100 including a computing device 106 coupled sensors 4202A, 4202B, 4202C, 4202, where the sensors are attached to a patient 4110. The computing system can include a display 4208 that can display various physiological parameters. The sensors 4202A, 4202B, 4202C, 4202 can collect various types of physiological data from the patient 4110 and transmit the data to the computing system via wires or wirelessly. Some example of the sensors 4202A, 4202B, 4202C, 4202 include, but not limited to, a rainbow acoustic monitoring sensor (RAM), 03 Regional Oximetry sensor, SpO2 sensor, a blood pressure sensor, an ECG sensor, and the like.

FIG. 3A shows a front perspective view of an example of a pulse oximeter sensor assembly 1202 that may be part of a sensor system environment. A reusable module 1250 can be a pairing device that can establish wireless connection with the computing device 1206. The disposable device 1220 can include the dock 1222 and the cable 1230 coupling the dock 1222 to the sensor 1240 (not shown).

The dock 1222 can include a strap 1308 that is coupled to a bottom portion of the dock 1222. The strap 1308 can loop around a patient (e.g., a wrist or an arm) to removably attach the dock 1222 to the patient. The dock 1222 can also include a strap loop 1302 having a slot for the strap 1308 to extend through. The strap 1308 can extend through the strap loop 1302 and loop around to removably attach the dock 1222 to the patient. The strap 308 can include a fastener 1310 disposed near a distal end of the strap 1308 that can interact with the strap 308 to fix the distal end of the strap 1308. The fastener 1310 can be located at a distal end of the strap 1308. The fastener 1310 can be located at other locations of the strap 1308. The dock can also include a retainer 1304 that holds the reusable module 1250 within the dock 1222 to maintain electrical connection between the reusable module 1250 and the dock 1222. Moreover, the dock 1222 can include a housing 1300 that can house the battery 1224 and the memory 1226.

The dock 1222 can include a cable retainer 1306 disposed on a side of the dock 222. The cable retainer 306 can be dimensioned and sized to retain the cable 1230. The cable retainer 1306 can be removably connected to the dock 1222. At least a portion of the cable retainer 1306 may be flexible to facilitate insertion of the cable 1230 into the cable retainer 1306. The cable retainer 1306 can advantageously limit movement of the cable 1230 to prevent possible tangling of cables of different sensor assemblies. The cable retainer 1306 can include a channel to through which the cable 1230 can extend. The channel of the cable retainer 1306 can be dimensioned such that the cable 1230 is snug within the channel, thereby limiting movement of the cable 1230.

FIG. 3B shows a front perspective view of an example of an ECG sensor 2310 that may be part of a sensor environment. The ECG device 2310 can be attached to different parts of the patient 4110 such as the patient's chest, back, arms, legs, neck, head, or other portions of the body of the patient. The ECG device 2310 can collect one or more types of patient physiological data and transmit the data to other monitoring systems or devices. The physiological data can be transmitted to other monitoring systems or devices via wires or various wireless communication protocols. For example, as discussed above, the ECG device 2310 can interact with the various other physiological devices and/or systems, such as a blood pressure monitors discussed herein and/or patient monitor 4106.

FIG. 3B illustrates an ECG device 2110 (also referred to herein as "ECG sensor"). ECG device 2110 can be attached to different parts of the patient 4110 such as the patient's chest, back, arms, legs, neck, head, or other portions of the body of the patient. An ECG device 2110 can be connected to the blood pressure monitor 2120 via cable 2105. For example, the connector 2105a of cable 2105 can connect to the connector port 2516 of the blood pressure monitor 2120. In some cases, connector 2105a is identical to connector 2107a of cable 2107. In such cases, ECG device 2110 can connect directly to the patient monitor 2130 via connection of connector 2105a to a connector port of the patient monitor 4106. This can advantageously provide flexibility in the connection of the ECG device 2110 when a blood pressure monitor is not included in system 100. In some variants, cable 2105 is permanently secured to ECG device 2110 at the connector port 2250. For example, an end of cable 2105 can be permanently hard-wired to a circuit board of the ECG device 2110 and thus can be not removably securable like connector 2105a.

The ECG device 2110 can detect electrical signals responsive to the patient's cardiac activity and can transmit such signals, and/or physiological parameters responsive to such signals, to other patient monitoring systems and/or devices. The detected signals and/or physiological parameters can be transmitted to other patient monitoring systems and/or devices via wires or various wireless communication protocols. For example, as discussed above, the ECG device 2110 can interact and/or be utilized along with other devices/sensors.

The ECG device 2110 can have the functional and/or computational capabilities to calculate physiological parameters (for example, heart rate, precise body temperature values, among others) using raw physiological data (for example, raw temperature data, raw ECG data responsive to patient cardiac activity, among others). In this regard, the ECG device 2110 can transmit raw, unprocessed electrical signals or physiological data, and/or processed, calculated physiological parameters to other patient monitoring devices and/or systems, such as those discussed elsewhere herein (for example, a blood pressure monitor and/or the patient monitor 4106).

FIG. 3C illustrates an example of the EEG hardware system 3200 that may be part of a sensor system environment. For example, an EEG hardware system 3200 can include the sensor 3210, adaptor 3230, the EEG-adaptor cable 3220, and the adaptor-monitor cable 3240. A sensor 3210 can include the L1 electrode 3102, the L2 electrode 3104, the R1 electrode 3106, the R2 electrode 3108, and the reference electrode 3112. However, other amounts of electrodes can be used. For example, four electrodes corresponding to L1, R1, ground, and reference can be used. The EEG sensor 3210 including the electrodes can be combined as a sensor package 3210.

The EEG hardware system 3200 can include an EEG-adaptor cable 220 for carrying the electrical signals from the EEG sensor 3210 to an adaptor 3230. The EEG adaptor cable 220 can include an interface 302 as shown in FIG. 3A. The interface 302 can be reusable and can removable connect mechanically and electrically to the EEG sensor 210 (which may be disposable in some examples).

The EEG hardware system 3210 can include an adaptor 3230 for interfacing with both the EEG sensor 3210 and a clinician device. The adaptor 3230 can be a hardware module including circuits and other hardware components for processing EEG signals. In an example, the adaptor 3230 can include one or more hardware processors, a memory, and power electronics. The hardware processor can be programmed to implement the processes described herein for analyzing EEG signals. The memory can store instructions that can be executed by the hardware processor. The memory can also store system parameters, including predetermined thresholds and conditions. The power electronics can include circuits for analog to digital conversion. The power electronics can also include filter circuitry for processing EEG signals. Some of the filters are stored as executable instructions and can be executed by the hardware processor. The adaptor can generate outputs based on the received EEG signals and transmit the generated output to the clinician device. In some examples, the hardware processor of the clinician device does not need to process any of the EEG signals. The adaptor 3230 and the clinician device can be coupled with the adaptor-monitor cable 3240. The adaptor-monitor cable 3240 can include an interface to connect to the clinician device. In some examples, the EEG hardware system 3200 does not include an adaptor 3230 and the EEG adaptor cable 3220 can directly connect to a clinician device. The clinician device can process the EEG signals and execute processes described herein instead of the adaptor. In some examples, the hardware processor of the clinician device can process the EEG signals and execute processes described herein in combination with the adaptor 3230.

The clinician device may be configured to pair with one or more sensors in the sensor system. In some examples, a clinician device can be a multi-parameter system for processing and analyzing sensor signals. The clinician device includes one or more hardware processors, a memory, a display, and power electronics. The hardware processors of the clinician device can be programmed to execute instructions stored in either an onboard memory of the adapter or the memory of the patient monitor. The clinician device can also include a display 4206 that can display parameters and graphs generated from the analysis of the received raw EEG signals or signals processed by the adaptor 3220.

C. Example Medical Coding Environment

Figure 4:
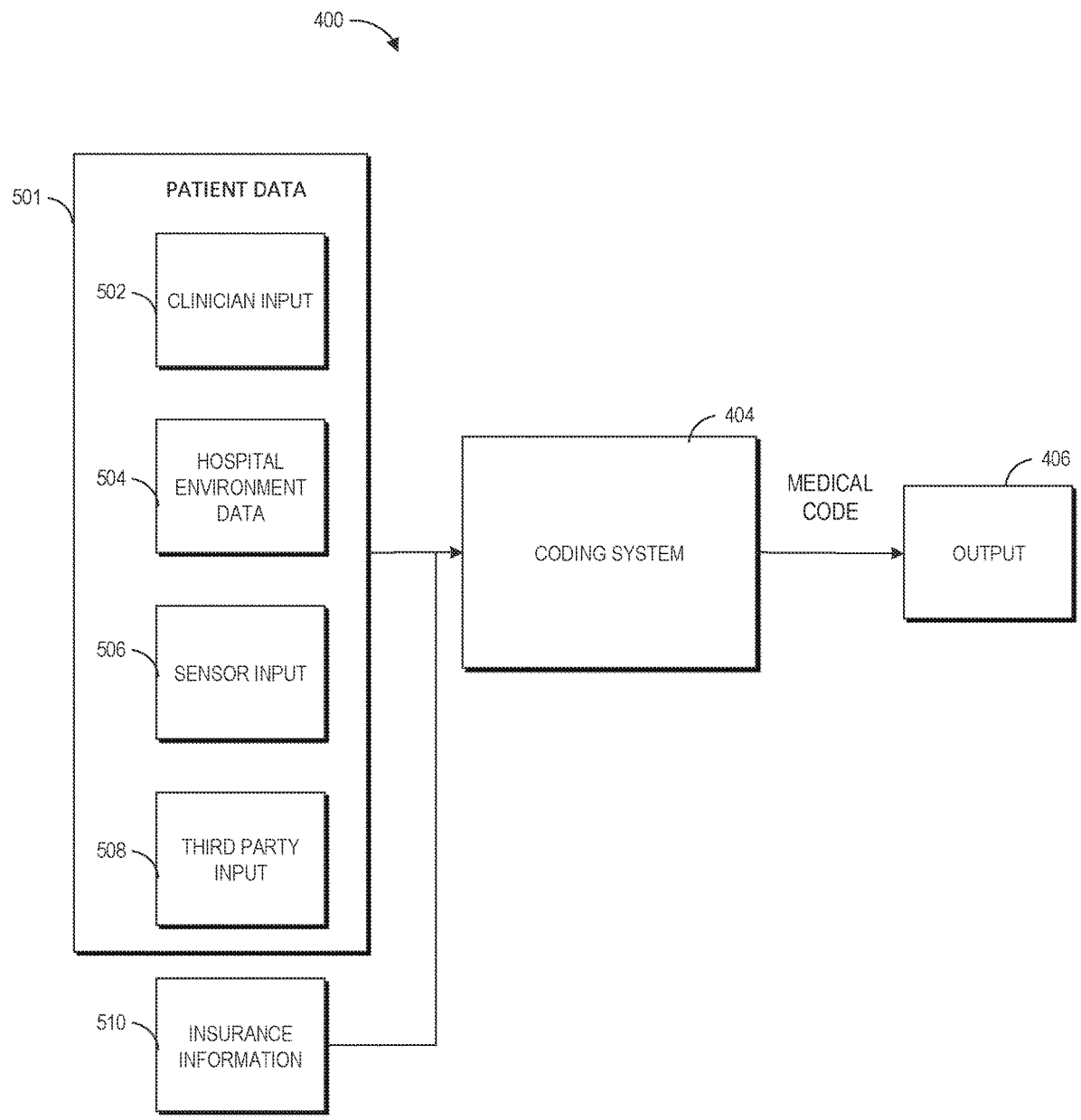
FIG. 4 illustrate an example coding environment.

FIG. 4 illustrates an example medical coding environment 400 that may help improve reimbursement rates and accuracy in medical coding. For example, a medical coding environment 400 can include patient data 501 and insurance information 510 transmitted to a coding system 404. The coding system 404 can generate a medical service code 404. The medical service code 404 can be transmitted to an output 406.

The patient data 501 can include clinician input 502, hospital environment data 504, sensor input 506, third party input 508, other patient data, or some combination thereof.

The clinician input 502 can include one or more notes or selections associated with a medical diagnosis, diagnosis code, service provided, procedure provided, treatment provided, service or other medical code, or other patient related information. For example, a clinician input can include patient symptoms, such as fever, swollen tonsils, and a sore throat. Additionally or alternatively, the clinician input can include one or more medical diagnoses and/or one or more diagnosis codes associated with one or more medical diagnoses (for example, 2020 ICD-10-CM Diagnosis Code J02.0 for streptococcal pharyngitis). In some examples, the clinician input can include one or more treatments, procedures performed, or service codes. For example, a clinician can include a note regarding prescribing antibiotics, respiratory diagnostic procedure, or other service performed or treatment applied. Additionally or alternatively, a clinician input can include other inputs related to a patient, such as a clinician observation that may or may not have an associated diagnosis or service code.

The clinician input 502 may be input into a clinician device. The clinician device may communicate the clinician input 502 to a storage location, such as an electronic medical record (EMR) associated with a patient.

The hospital environment data 504 can include information associated with a patient's clinical environment that may or may not result from a clinician interaction. For example, hospital environment data 504 can include the length of a patient's stay at a hospital, routine patient monitoring, use of hospital resources, other hospital data associated with a medical service or treatment to be billed to a payor, the like or some combination thereof.

The hospital environment data 504 may be data that is manually input to a patient's record by, for example, a user having access to patient information, such as a clinician or patient. In some examples, the hospital environment data 504 may be data that is stored in a local or cloud based database, such as an electronic medical record (EMR) or other source of stored information associated with the patient. In some examples, the hospital environment data 504 that may be determined, updated, or otherwise associated with data automatically, semi-automatically, or manually obtained or stored through connected clinical devices. In some examples, the hospital environment data 504 may include a combination of such inputs. For example, the hospital environment data 504 can include a length of a hospital stay. When a patient is hooked up to a monitoring device in a hospital, the monitoring device may communicate that the patient's stay has started. Additionally or alternatively, a clinician, such as a nurse, may input that the patient has been discharged or started. In some examples, decision logic may arbitrate inputs. For example, a sensor input may indicate a patient is still checked in to a hospital while a clinician input may indicate that the patient's stay is complete, decision logic may determine that the patient is still checked in despite the clinician input.

The sensor input 506 may be input from one or more sensors or other machines configured to collect physiological data from the patient. For examples, a patient may have an MRI taken. The MRI machine may automatically or semi-automatically record the imaged information and length of time the patient used the MRI machine into a patient's record. In another example, a patient monitor may monitor a patient's sedative state during a surgical procedure. The patient monitor may input information associated with a patient's sedative state, such as that a patient was sedated during a certain period of time.

The sensor input 506 can be input manually, automatically, or semi-automatically into a patient's record. For example a sensor may directly or indirectly communicate with a memory storing a patient record. In another example, a sensor output may be recorded or noted by a user or clinician and input into a device that may communicate with a memory storing a patient record.

The third party input 508 may be input from a third party associated with a patient. For example, the third party input 508 can include third party patient data, such as health related data from a patient's mobile device, wearable device, another data collection device or a data aggregator. Additionally or alternatively, the third party input 508 can include data from third parties that may be associated with the clinician who provide services to the patient. For example, a third party may perform a diagnostic assessment, such as a blood or urine analysis. The third party may bill the hospital or clinical care provider and the hospital or clinical care provider may apply for reimbursement from the payor.

The third party input 508 can be input manually or automatically into a patient's record. For example a third party, third party device, or third party application may directly or indirectly communicate with a memory storing a patient record. In another example, a third party input may be recorded or noted by a user or clinician and input into a device that may communicate with a memory storing a patient record.

In addition or in the alternative to patient data 501, an environment 400 can include insurance information 510. Insurance information 510 can include an identity of a payor for a patient, patient plan information with a payor, and payor specific information. For example, a patient may have a particular plan with a specific payor. The plan may have coverage limits, a patient deductible, billing preferences (such as per procedure or itemized billing), or other plan specific information. The insurance information 510 can include such plan information. Additionally or alternatively, the insurance information 510 can include payor specific information such as billing codes specific to the payor or other associated billing information. In some cases, the billing codes may be associated with medical codes, such as service codes or diagnostic codes collected with the patient data 501.

Other insurance information 510 can include payor specific information such as historical payor specific data. For example, a payor may have a history of rejecting or accepting certain treatments or service/billing codes for certain diagnoses or diagnosis codes for the purposes of reimbursement. Insurance information 510 can include this historical data. In some examples, this historical data can include data of reimbursement rejections or acceptances specific to the patient. In other examples, the historical data can include data of reimbursement rejections or acceptances across multiple patients in, for example, an insurer's database or a hospital's database. Additionally or alternatively, the historical payor specific data can include an amount of reimbursement or other information associated with reimbursements, such as amount of time to obtain a reimbursement for a particular medical code or for a particular combination of patient data.

The patient data and insurance information can be analyzed by a coding system 404. The coding system 404 can be implemented by one or more hardware processors. The one or more hardware processors can include processors associated with a patient monitoring device, clinician device, third party device, medical record server, other computing device, the like or some combination thereof.

The coding system 404 may produce a medical code, such as a billing code particular to a payor, through one or more coding processes, such as described with reference to FIG. 5. The coding system 404 may apply one or more machine learning processes to analyze patient data 501 and/or insurance information to produce a medical code. In some examples, a coding system can utilize one or more classifiers trained to determine a medical code or diagnosis code and treatment code pair most likely to provide the greatest reimbursement based on the patient data and insurance information.

A medical code generated by the coding system can be transmitted to an output 406. The output 406 can include a display, a third party device, a database, a payor, a payor's device, the like, or some combination thereof. In some examples, the generated medical code can be reviewed by a user or another process for accuracy prior to compiling for billing a payor. In another example, the generated medical code can be sent directly to the payor.

D. Example Machine Learning

In some examples, a coding system 404, such as illustrated in FIG. 4, may include one or more code recognizers. The one or more code recognizers may be configured to crawl through received data (for example, sensor data, insurance data, clinician input information, or other input data) and recognize or classify diagnosis codes or billing codes, tag data, attach semantic information to data, or perform other processes related to medical billing. In some examples, the one or more code recognizers may be configured using machine learning techniques to analyze input data with the help of training data. The training data may include patient, insurance, or other billing or medical data collected over time and a corresponding billing or diagnosis code.

A code recognizer may be configured to determine a billing and/or diagnosis code, recognize errors in input data, identify likely pairs of diagnosis and services provided, detect billing or medical events (for example, start, end, and/or duration of a provided service, such as a start of a surgical procedure), index data, and others. One or more algorithms may be used to perform these tasks.

Code recognitions can additionally or alternatively be performed by a variety of machine learning algorithms. Once trained, the machine learning algorithm can be stored by the HMD. Some examples of machine learning algorithms can include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms (such as e.g., support vector machine, k-nearest neighbors algorithm, Naive Bayes, neural network (including convolutional or deep neural networks), or other supervised/unsupervised/semi-supervised models, etc.), and so forth.

In some implementations, individual models can be customized for individual data sets. For example, a coding system may can generate, access, or store a base model. The base model may be used as a starting point to generate additional models specific to a data type (e.g., for example, a likelihood of reimbursement for a patient with a specific diagnosis having a particular type of insurance), a data set (e.g., a set of additional data obtained for a patient), conditional situations, or other variations. In some implementations, the wearable HMD can be configured to utilize a plurality of techniques to generate models for analysis of the aggregated data. Other techniques may include using predefined thresholds or data values.

Based on the input information, the code recognizers may recognize billing codes, service codes, procedures, services, or events associated with a service code, diagnoses, diagnostic codes, likelihood of reimbursement for one or more codes, or a combination thereof. For example, if a code recognizer recognizes a pattern in input data associated with a likelihood of a service being performed, the system may attach some semantic information (e.g., a clinician inputs information to a sensor device to begin monitoring a patient for anesthesia, the system may recognize a service event associated with anesthesia). In another example, if the code recognizer recognizes a set of inputs as a pregnancy diagnosis code and an input and a service code associated with a pregnancy test, the system may identify a high likelihood of reimbursement. In contrast, if the code recognizer identifies a service code associated with a service, such as a pregnancy test, and identifies patient information that seems incompatible with the service code (based on historical data or other training information), such as that the patient is genetically male, the code recognizer may identify a low likelihood of reimbursement. Over time the training data may grow as the system (which may reside locally or may be accessible through a wireless network) accumulates more data. Once codes are recognized, the information may be transmitted to one or more clinician devices.

E. Example Coding Process

Figure 5:
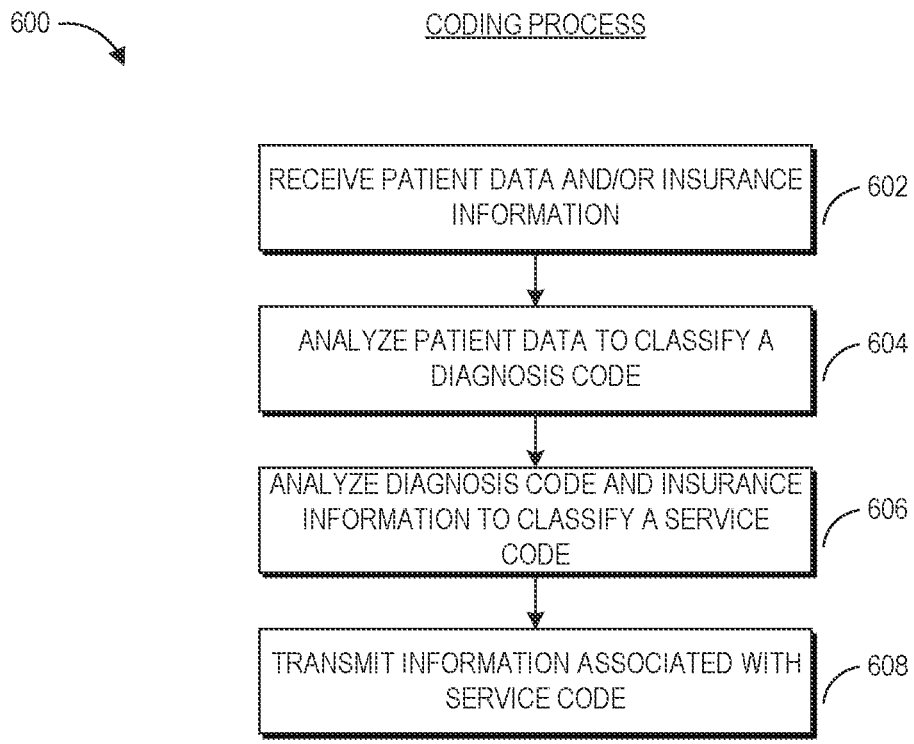
FIG. 5 illustrates an example coding process that may be part of an example coding environment.

FIG. 5 illustrates an example coding process 600 that may be part of a coding system 404 and/or use a code recognizer, such as described above. The coding process may include patient information and insurance information inputs and produce one or more billing or service codes.

At a block 602, a coding system 404 may receive patient data and/or insurance information. In some examples, a coding system 404 may retrieve or access patient data from a database. For example, the coding system 404 can access a patient EMR to access patient data stored in the EMR. In some examples, a coding system 404 may retrieve or access insurance information from a payor, clinician records, or a patient's EMR.

At a block 604, a coding system 404 can utilize a diagnosis code recognizer, such as a machine learning classifier, to analyze patient data to determine a diagnosis code appropriate for the patient data and that is most likely to provide a reimbursement with a proposed or provided treatment. For example a coding system 404 may analyze the patient input to classify or categorize a group of patient symptoms or other set of patient information into a suggested diagnosis code. In some examples, the coding system 404 may suggest the diagnosis code to a clinician for verification or produce a number of possible diagnosis codes with associated confidence values for selection by a clinician, coder, or the coding system in a later step in the coding process 600.

Additionally or alternatively, a diagnosis code recognizer, such as a machine learning classifier, can analyze an input diagnosis code for accuracy. For example, a clinician may have put in a diagnosis code associated with a broken wrist accidentally as opposed to a diagnosis code for an infection. Other patient data, such as a treatment option (of, for example, antibiotics) and other inputs associated with a patient, such as patient symptoms recorded by the clinician, physiological sensors, or other sources of patient data may indicate that the diagnosis code is incorrect. The diagnosis code recognizer, such as a machine learning classifier, may identify and determine that there is a high probability of an incorrect diagnosis code and accordingly, a low probability of reimbursement associated with the recorded diagnosis and treatment pair. An output, in some examples, a diagnosis code recognizer, such as a machine learning classifier, may determine an accuracy or confidence score associated with a selected diagnosis code.

In some examples, a coding system 404 may verify a diagnosis code and/or present options for a candidate diagnosis code based on the input information. For example, the coding system 404 may determine that there is a high likelihood of error in an input diagnosis code. In some examples, the likelihood of error may be determined using the diagnosis code recognizer. In one example, if a clinician inputs a diagnosis of pregnancy or other genetically female specific disease and the input information indicates the patient is genetically male, a coding system 404 may flag an error. The coding system 404 may output an alert to a clinician device or annotate a medical record to note the likelihood of error. In some examples, a coding system 404 may provide a plurality of candidate diagnosis codes based on input information. For examples, input information may include, but is not limited to, patient demographic information and clinician notes on patient symptoms or the like. In one example, if a clinician indicates that a patient has a sore throat and fever, a coding system 404 may generate a plurality of candidate diagnosis codes associated with disease with a sore throat and fever.

The diagnosis code recognizer, such as a machine learning classifier, may be trained using patient specific data, data from multiple patients, diagnostic guidelines, other source of information associated with medical diagnoses, the like, or some combination thereof. In some examples, the diagnosis code recognizer may utilize insurance information in addition to patient data to identify an appropriate diagnosis code for the patient data. In some examples, training data may include historical medical billing data, such as rejected and accepted medical service codes that may be paired with diagnostic data, such as medical record data associated with a provided service.

At a block 606, a coding system 404 can utilize a service code recognizer, such as a machine learning classifier, to analyze a diagnosis code, such as the code determined in step 604, and insurance information to help identify a service code that is appropriate for the applied treatment and that is most likely to prove a reimbursement for the proposed or applied treatment. In some examples, the coding system 404 can suggest one or more optimal or near optimal service codes for the treatment plan or diagnosis associated with a patient in order to improve accuracy of billing and likelihood of reimbursement. For example, a coding system 404 can analyze the diagnosis code and/or patient data along with the insurance information to suggest a service code to a clinician, coder, or other user that is appropriate and most likely to be reimbursed according to the provided data. The clinician or other user can then utilize the suggestion as another piece of information to consider in deciding a treatment plan. In another example, some services or procedures may be able to be categorized into more than one code. A service code recognizer, such as a machine learning classifier, may help determine a preferred service code to record in association with that particular procedure or service. An output of the service code recognizer may be a probability of reimbursement, alert associated with probability of reimbursement, a suggested service code, or other information associated with a service code. Advantageously, use of the service code recognizer may allow a user to preemptively identify potential issues with a service code, such as an inconsistency with a place of service, patient age, gender, insurance coverage or the like and fix potential issues or adjust treatment prior to rejection of a claim by a payor.

The service code recognizer may be trained using a set of training data that may be specific to the patient, diagnosis code, or across multiple patients or diagnosis codes. For example, a coding system can analyze a clinician input regarding a diagnosis and analyze a history of approved service codes associated with that diagnosis code. If the service code in conjunction with the diagnosis code or other patient data is unlikely, based on the training data to be reimbursed, the service code recognizer may classify a particular service code and diagnosis code pair as not optimal. Conversely, if the service code in conjunction with the diagnosis code or other patient data is more likely based on the training data to be reimbursed, the service code recognizer may classify a particular service code and diagnosis code pair as more optimal. In some examples, training data may include historical medical billing data, such as rejected and accepted medical service codes that may be paired with diagnostic data, such as medical record data associated with a provided service.

At a block 608, the coding system 404 may transmit a service code or information associated with a service code to an output device. For example, the coding system 404 may transmit a suggested service code or a probability of reimbursement associated with a service code. In some examples, the coding system 404 may transmit an alarm if a probability of reimbursement associated with a service code falls below a threshold value. In some examples, the coding system 404 may transmit a suggested service code to a clinician, coder, or other user for evaluation and selection. In some examples, the coding system 404 may transmit a selected service code to a clinician, coder, or other user for user in billing. In some examples, the coding system 404 may transmit a service code directly or indirectly to a payor.

F. Examples

Disclosed herein are example aspects of the automated medical coding system described. Any of the described examples in this disclosure may be combined.

In a 1st example, a system for improving accuracy of medical coding can include:
- a non-transitory memory configured to store a machine learning classifier,
  wherein the machine learning classifier is configured to identify a service code associated with a threshold probability of reimbursement by a payor, and
  wherein the machine learning classifier is trained using historical reimbursement data associated with a plurality of patient records; and
- one or more hardware processors in communication with the non-transitory memory, the one or more hardware processors configured to:
- receive patient information comprising at least one of: physiological parameters obtained from the at least one physiological sensor and clinician input,
  wherein the clinician input comprises diagnosis data or treatment data;
- access insurance information associated with the patient comprising at least one of: plan coverage and a plurality of service codes;
- identify a diagnosis code associated with the patient based on the patient information; and
- analyze the patient information and the insurance information to determine, using the at least one machine learning classifier, at least one service code associated with a threshold probability of reimbursement by the payor.

In a 2nd example, a system for improving accuracy of medical coding, the system comprising:

a non-transitory memory configured to store a machine learning classifier,
wherein the machine learning classifier is configured to identify a service code associated with a threshold probability of reimbursement by a payor, and
wherein the machine learning classifier is trained using historical reimbursement data associated with the payor; and
one or more hardware processors in communication with the non-transitory memory, the one or more hardware processors configured to:
receive patient information from comprising at least one of:
one or more physiological parameters obtained from the at least one physiological sensor, or clinician input;
determine insurance information of the patient;
analyze, using the at least one machine learning classifier, the patient information and the insurance information to determine at least one service code associated with a threshold probability of reimbursement by the payor and a confidence score associated with the at least one service code; and
output the at least one service code, based on the confidence score, to a clinician device.

In a 2nd example, the system of Example 1, wherein the historical reimbursement data is associated with a plurality of patient records.

In a 3rd example, the system of Example 1, wherein the historical reimbursement data is associated with a patient diagnosis or patient diagnosis code.

In a 4th example, the system of Example 1, wherein the clinician input comprises diagnosis data or treatment data.

In a 5th example, the system of Example 1, wherein the insurance information comprises plan coverage associated with an insurance plan of the patient.

In a 6th example, the system of Example 1, wherein the clinician device comprises a computing device.

In a 7th example, the system of Example 6, wherein the clinician device comprises a mobile computing device.

In an 8th example, the system of Example 6, wherein the clinician device comprises the at least one physiological sensor or a patient monitor.

In a 9th example, the system of Example 1, wherein the one or more hardware processors are configured to select a service code of a plurality of service code with a highest confidence score and wherein to output the at least one service code, the one or more hardware processors are configured to output the service code with the highest confidence score.

In a 10th example, the system of Example 1, wherein the one or more hardware processors are configured to output a plurality of service codes and confidence scores.

In an 11th example, the system of Example 10, wherein the one or more hardware processors are configured to accept a selection of a service code of the plurality of service codes and store the selection of the service code to a database.

In a 12th example, the system of Example 11, wherein the one or more hardware processors are configured to submit the selection of the service code to the payor.

In a 13th example, a system for improving accuracy of medical coding, the system comprising:
a non-transitory memory configured to store a classifier,
wherein the classifier is configured to identify a service code associated with a threshold probability of reimbursement by a payor, and
wherein the classifier is trained using machine learning with historical reimbursement data associated with the payor; and
one or more hardware processors in communication with the non-transitory memory, the one or more hardware processors configured to:
receive patient information from comprising at least one of:
one or more physiological parameters obtained from the at least one physiological sensor, or clinician input;
determine insurance information of the patient;
receive a service code input and a diagnosis input from a clinician device;
determine, using the at least one classifier, a likelihood of reimbursement associated with the service code input based on the diagnosis input; and
output the likelihood of reimbursement to a clinician device.

In a 14th example, the system of Example 13, wherein the one or more hardware processors are configured to determine, using the at least one classifier, a plurality of candidate service codes and associated confidence scores.

In a 15th example, the system of Example 14, wherein the one or more hardware processors are configured to output at least some of the plurality of candidate service codes to the clinician device.

In a 16th example, the system of Example 15, wherein the one or more hardware processors are configured to receive, from the clinician device, an updated service code based on the plurality of candidate service codes.

In a 17th example, the system of Example 16, wherein the one or more hardware processors are configured to submit the updated service code to the payor.

In an 18th example, the system of Example 13, wherein the clinician input comprises diagnosis data or treatment data.

In a 19th example, the system of Example 13, wherein the insurance information comprises plan coverage associated with an insurance plan of the patient.

In a 20th example, the system of Example 13, wherein the clinician device comprises a computing device.

In a 21st example, a system for improving accuracy of medical coding, the system comprising:
a non-transitory memory configured to store a classifier,
wherein the classifier is configured to identify a diagnosis code based on a plurality of patient input information, and
wherein the classifier is trained using machine learning with historical data associated with a plurality of patient data; and
one or more hardware processors in communication with the non-transitory memory, the one or more hardware processors configured to:
receive patient information from comprising at least one of:
one or more physiological parameters obtained from the at least one physiological sensor, or clinician input;
receive a diagnosis code input and a diagnosis input from a clinician device;
determine, using the at least one classifier, a likelihood of accuracy of the diagnosis code based on the diagnosis code input and the diagnosis input; and
output the likelihood of accuracy to a clinician device.

In a 22nd example, the system of Example 21, wherein the one or more hardware processors are configured to determine, using the at least one classifier, a plurality of candidate diagnosis codes and associated confidence scores.

In a 23rd example, the system of Example 21, wherein the one or more hardware processors are configured to output at least some of the plurality of candidate diagnosis codes to the clinician device.

In a 24th example, the system of Example 21, wherein the one or more hardware processors are configured to receive, from the clinician device, an updated diagnosis code based on the plurality of candidate diagnosis codes.

In a 25th example, the system of Example 24, wherein the one or more hardware processors are configured to submit the updated diagnosis code to the payor.

In a 26th example, the system of Example 21, wherein the clinician input comprises diagnosis data or treatment data.

In a 27th example, the system of Example 21, wherein the insurance information comprises plan coverage associated with an insurance plan of the patient.

In a 28th example, the system of Example 21, wherein the clinician device comprises a computing device.

In a 29th example, the system of Example 21, wherein the one or more hardware processors are configured to receive a service code input.

In a 30th example, the system of Example 29, wherein the one or more hardware processors are configured to determine a likelihood of reimbursement by a payor based on the diagnosis code and the service code input.

In a 31st example, the system of Example 30, wherein to determine a likelihood of reimbursement, the one or more hardware processors are configured to analyze the diagnosis code and the service code using at the at least one classifier.

In a 32nd example, the system of Example 30, wherein the one or more hardware processors are configured to output the likelihood of reimbursement to the clinician device.

In a 33rd example, a method of any of the above examples.

In a 34th example, a system or method of training a classifier for any of the above examples.

G. Terminology

Many other variations than those described herein can be apparent from this disclosure. For example, depending on the embodiment, certain acts, events, or functions of any of the algorithms described herein can be performed in a different sequence, can be added, merged, or left out altogether (for example, not all described acts or events can be necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

Not necessarily all such advantages are achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality can be implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A hardware processor can be a microprocessor, but in the alternative, the processor can be a controller, microcontroller, or state machine, combinations of the same, or the like. A processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may." "for example," and the like, unless specifically stated otherwise, or otherwise understood within the context as used, are generally intended to convey that certain embodiments include, while other embodiments do not include, certain features, elements and/or states. Thus, such conditional language is not generally intended to imply that features, elements and/or states are in any way may required for one or more embodiments or that one or more embodiments necessarily include logic for deciding, with or without author input or prompting, whether these features, elements and/or states are included or are to be performed in any particular embodiment. The terms "comprising." "including." "having." and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" mechanism one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, can be otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments may require at least one of X, at least one of Y, or at least one of Z to each be present.

Unless otherwise explicitly stated, articles such as "a" or "an" should generally be interpreted to include one or more described items. Accordingly, phrases such as "a device configured to" is intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it is understood that various omissions, substitutions, and changes in the form and details of the devices or algorithms illustrated can be made without departing from the spirit of the disclosure. As is recognized, certain embodiments of the inventions described herein can be embodied within a form that does not provide all of the features and benefits set forth herein, as some features can be used or practiced separately from others.

The invention claimed is:

1. A system for improving accuracy of medical coding, the system comprising:
   a patient monitoring device configured to communicate with at least one treatment device configured to administer a medical treatment to the patient;
   a non-transitory memory configured to store a plurality of machine learning classifiers comprising at least a first machine learning classifier and a second machine learning classifier,
   wherein the first machine learning classifier of the plurality of machine learning classifiers is configured to identify a service code associated with a threshold probability of reimbursement by a payor,
   wherein the first machine learning classifier is trained using historical reimbursement data associated with the payor,
   wherein the second machine learning classifier of the plurality of machine learning classifiers is configured to determine a likelihood that a diagnosis code corresponding to the service code is accurate,
   wherein the second machine learning classifier is trained using diagnostic data associated with rejected and accepted medical service codes, and
   wherein the first machine learning classifier is configured to transform the historical reimbursement data associated with the payor and information associated with the patient into the threshold probability of reimbursement by the payor; and
   one or more hardware processors in communication with the non-transitory memory, the one or more hardware processors configured to:
      receive identification information corresponding to the patient from a clinician device;
      associate the patient monitoring device with the patient based on the identification information;
      receive patient data from the patient monitoring device, wherein the patient data is representative of at least one or more symptoms of the patient and a diagnosis, and wherein the one or more symptoms and diagnosis are input by a clinician;
      automatically store at least the patient data in an electronic medical record system based at least in part on the identification information;
      determine insurance information of the patient;
      analyze, using the second machine learning classifier, the patient data to determine a likelihood of accuracy for the diagnosis code, wherein the diagnosis code is input by a clinician;
      determine, using the second machine learning classifier, that the diagnosis code is not accurate based on a determination that the diagnosis code input is not associated with the diagnosis input;
      determine, using the second machine learning classifier, a plurality of candidate diagnosis codes based at least in part on the symptoms of the patient, wherein each candidate diagnosis code is associated with a disease that comprises said symptoms,
      for each candidate diagnosis code, using the second machine learning classifier, analyze the patient data to determine a likelihood of accuracy for the candidate diagnosis code;
      suggest, using the second machine learning classifier, at least some of the candidate diagnosis codes based on a determination that one or more candidate diagnosis codes are associated with the diagnosis input;
      receive a selection of an updated diagnosis code from the clinician device, wherein the updated diagnosis code is selected from the suggested candidate diagnosis codes;
      analyze, using the first machine learning classifier, the patient data, the updated diagnosis code, and the insurance information to determine at least one service code associated with a threshold probability of reimbursement by the payor and a confidence score associated with the at least one service code; and
      output the at least one service code, based on the confidence score, to the clinician device, wherein the service code is a basis for the clinician in deciding a treatment plan for the patient.

2. The system of claim 1, wherein the historical reimbursement data is associated with a plurality of patient records.

3. The system of claim 1, wherein the historical reimbursement data is associated with a patient diagnosis or patient diagnosis code.

4. The system of claim 1, wherein the insurance information comprises plan coverage associated with an insurance plan of the patient.

5. The system of claim 1, wherein the clinician device comprises a computing device.

6. The system of claim 5, wherein the clinician device comprises a mobile computing device.

7. The system of claim 5, wherein the clinician device comprises a patient monitor.

8. The system of claim 1, wherein the one or more hardware processors are configured to select a service code of a plurality of service code with a highest confidence score and wherein to output the at least one service code, the one or more hardware processors are configured to output the service code with the highest confidence score.

9. The system of claim 1, wherein the one or more hardware processors are configured to output a plurality of service codes and confidence scores.

10. The system of claim 9, wherein the one or more hardware processors are configured to accept a selection of a service code of the plurality of service codes and store the selection of the service code to a database.

11. The system of claim 10, wherein the one or more hardware processors are configured to submit the selection of the service code to the payor.

12. A system for improving accuracy of medical coding, the system comprising:
 a non-transitory memory configured to store at least one classifier,
  wherein the at least one classifier is configured to determine a likelihood that a diagnosis code corresponding to a service code is accurate, and
  wherein the at least one classifier is trained using machine learning with diagnostic data associated with rejected and accepted medical service codes; and
 one or more hardware processors in communication with the non-transitory memory, the one or more hardware processors configured to:
  receive identification information corresponding to a patient from a clinician device;
  associate a patient monitoring device with the patient based on the identification information, the patient monitoring device configured to receive treatment information associated with a treatment device coupled to the patient, wherein the treatment information is representative of at least one or more symptoms of the patient and a diagnosis;
  receive patient data from the patient monitoring device, wherein the patient data comprises at least the treatment information;
  automatically store the patient data in an electronic medical record system based at least in part on the identification information;
  determine insurance information of the patient;
  receive a diagnosis code input from the clinician device;
  analyze, using the at least one classifier, the patient data to determine a likelihood of accuracy for the diagnosis code input;
  determine, using the at least one classifier, that the diagnosis code input is not accurate based on a determination that the diagnosis code input is not associated with the diagnosis;
  determine, using the at least one classifier, a plurality of candidate diagnosis codes based at least in part on the symptoms of the patient, wherein each candidate diagnosis code is associated with a disease that comprises said symptoms,
  for each candidate diagnosis code, using the at least one classifier, analyze the patient data to determine a likelihood of accuracy for the candidate diagnosis code;
  suggest, using the at least one classifier, at least some of the candidate diagnosis codes based on a determination that one or more candidate diagnosis codes are associated with the diagnosis; and
  receive a selection of an updated diagnosis code from the clinician device,
   wherein the updated diagnosis code is selected from the suggested candidate diagnosis codes,
   wherein the updated diagnosis code is used to determine a candidate service code that is output to the clinician device, the candidate service code associated with a threshold probability of reimbursement by a payor, and
   wherein the candidate service code is a basis for the clinician in deciding a treatment plan for the patient.

13. The system of claim 12, wherein the one or more hardware processors are configured to determine, using the at least one classifier, a plurality of candidate service codes and associated confidence scores.

14. The system of claim 13, wherein the one or more hardware processors are configured to output at least some of the plurality of candidate service codes to the clinician device.

15. The system of claim 14, wherein the one or more hardware processors are configured to receive, from the clinician device, an updated service code based on the plurality of candidate service codes.

16. The system of claim 15, wherein the one or more hardware processors are configured to submit the updated service code to the payor.

17. The system of claim 12, wherein the clinician input comprises diagnosis data or treatment data.

18. The system of claim 12, wherein the insurance information comprises plan coverage associated with an insurance plan of the patient.

19. The system of claim 12, wherein the clinician device comprises a computing device.

* * * * *